(12) United States Patent
Ranga et al.

(10) Patent No.: US 12,031,115 B2
(45) Date of Patent: Jul. 9, 2024

(54) DEVICES AND METHODS FOR THREE-DIMENSIONAL GROWTH OF CELLS

(71) Applicant: Katholieke Universiteit Leuven, Leuven (BE)

(72) Inventors: Adrian Ranga, Ixelles (BE); Sergii Grebeniuk, Heverlee (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 1010 days.

(21) Appl. No.: 16/965,878

(22) PCT Filed: Jan. 30, 2019

(86) PCT No.: PCT/EP2019/052249
§ 371 (c)(1),
(2) Date: Jul. 29, 2020

(87) PCT Pub. No.: WO2019/149752
PCT Pub. Date: Aug. 8, 2019

(65) Prior Publication Data
US 2021/0054322 A1 Feb. 25, 2021

(30) Foreign Application Priority Data
Jan. 31, 2018 (GB) ..................................... 1801582

(51) Int. Cl.
*C12M 1/12* (2006.01)
*B01L 3/00* (2006.01)
(Continued)

(52) U.S. Cl.
CPC ....... *C12M 23/16* (2013.01); *B01L 3/502715* (2013.01); *C12M 25/14* (2013.01);
(Continued)

(58) Field of Classification Search
CPC ...... C12M 23/16; C12M 25/14; C12M 23/20; C12M 25/10; C12M 29/04; C12M 29/16;
(Continued)

(56) References Cited

U.S. PATENT DOCUMENTS

| 9,452,239 B2 * | 9/2016 | West | ................ A61L 27/56 |
| 2011/0033887 A1 * | 2/2011 | Fang | .................. B81C 99/0095 |
| | | | 73/1.01 |

(Continued)

FOREIGN PATENT DOCUMENTS

WO 2016141137 A1 9/2016

OTHER PUBLICATIONS

International Search Report in reference to co-pending European Application No. PCT/EP2019/052249 filed Jan. 30, 2019.
(Continued)

*Primary Examiner* — Liban M Hassan
(74) *Attorney, Agent, or Firm* — Dinsmore & Shohl LLP

(57) ABSTRACT

The invention relates to devices for the culture of cellular aggregates A comprising a three-dimensional network of interconnected vessels of a biocompatible liquid- and gas-permeable photo polymerised material, wherein the three-dimensional network is connected to a plurality of inlets and a plurality of outlets for the delivery of liquids, and overlayed with a secondary hydrogel network wherein the cellular aggregates are embedded. Herein defined vessels within the three-dimensional network are blocked, thereby defining at least one spatially segregated network within and structurally in contact with the three-dimensional network, wherein the at least one spatially segregated network is connected to a separate inlet and a separate outlet, allowing the supply of a liquid to a subregion within the three-dimensional network.

11 Claims, 2 Drawing Sheets

(51) Int. Cl.
  *C12M 3/06* (2006.01)
  *C12N 5/00* (2006.01)
(52) U.S. Cl.
  CPC ...... *C12N 5/0075* (2013.01); *B01L 2300/163* (2013.01); *C12N 2513/00* (2013.01); *C12N 2533/54* (2013.01)
(58) Field of Classification Search
  CPC ......... B01L 3/502715; B01L 2300/163; C12N 5/0075; C12N 2513/00; C12N 2533/54
  See application file for complete search history.

(56) References Cited

U.S. PATENT DOCUMENTS

2016/0130543 A1    5/2016   Daniele et al.
2017/0009194 A1*   1/2017   Golway ............... C12N 5/0691

OTHER PUBLICATIONS

Written Opinion in reference to co-pending European Application No. PTC/EP2019/052249 filed Jan. 30, 2019.
Birey, et al., "Assembly of functionally integrated human forebrain spheroids", Nature Article, vol. 545, pp. 54-77, May 4, 2017.
Demers, et al., "Development-on-chip: in vitro neural tube patterning with a microfluidic device", Stem Cells and Regeneration, pp. 1884-1892, 2016.
Freiman, et al., "Adipose-derivedendothielial and mesenchymal stem cells enhance vascular network formation on three-dimensional constructs in vitro", Stem Cell Research & Therapy, pp. 1-12, 2016.
Griffith, et al., "Capturing complex 3D tissue physiology in vitro", Focus on Modelling Cellular Systems, Nature Reviews, vol. 7, pp. 211-224, Mar. 2006.
Kleinman, et al., "Matrigel: Basement membrane matrix with biological activity", Seminars in Cancer Biology, vol. 15, pp. 378-386, 2005.
Langer, et al., "Designing materials for biology and medicine", Nature Review Article, vol. 428, pp. 487-492, Apr. 2004.
Levenberg, et al., "Engineering vascularized skeletal muscle tissue", Nature biotechnology letters, vol. 23, No. 7, pp. 879-884, Jul. 2005.
Lutolf, et al., "Repair of bone defects using synthetic mimetics of collagenous extracellualr matrices", Nature Research Article, vol. 21, pp. 513-518, May 2003.
Lutolf, et al., "Designing materials to direct stem-cell fate", Nature Review Insight, vol. 462, pp. 433-441, Nov. 26, 2009.
Miller, et al., "Rapid casting of patterned vascular networks for perfusable engineered three-dimensional tissues", Nature Materials Letters, vol. 11, pp. 768-774, Sep. 2012.
Ranga, et al., "Drug discovery through stem cell-based organoid models", Advanced Drug Delivery Reviews, pp. 19-28, 2014.
Zagorski, et al., "Decoding of position in the developing neural tube from antiparallel morphogen gradients", Research Report, pp. 1379-1383, Jun. 30, 2017.
Turner, et al., "Organoids and the genetically encoded self-assembly of embryonic stem cells", Prospects and Overviews, pp. 181-191, 2015.

* cited by examiner

DEVICES AND METHODS FOR THREE-DIMENSIONAL GROWTH OF CELLS

CROSS REFERENCES TO RELATED APPLICATIONS

This application is a national-stage application under 35 U.S.C. § 371 of International Application PCT/EP2019/052249, filed Jan. 30, 2019, which International Application claims benefit of priority to Great British Patent Application No. 1801582.6, filed Jan. 31, 2018.

TECHNICAL FIELD

The invention relates to methods and devices from growing 3D aggregates of cells. The invention further relates to photopolymerised materials such as hydrogels.

BACKGROUND

The engineering of biomimetic tissues in vitro is of fundamental importance for regenerative medicine applications. A more immediate use of in vitro models is in the process of drug discovery. A key reason for failures of drug candidates in human clinical trials is the over-simplicity of widely deployed in vitro models, and conversely, the important genetic, physiological and structural differences between in-vivo animal model and human physiology.

In order to overcome these important limitations, human organoids have been described as potentially transformational new model systems. Organoids are multi-cellular structures composed of multiple cell types which self-organize in vitro to form tissue-like structures with many characteristics of in-vivo organs. Derived from pluripotent stem cells or self-renewing tissue progenitor stem cells, organoids have been generated for an increasing variety of organs, including intestinal, kidney, brain, liver and retinal organoids. Derivation methods are specific to each of these systems, with a focus on the recapitulation of endogenous developmental processes.

In contrast to traditional two dimensional (2D) cell culture models which bear little physical, molecular, or physiological similarity to their tissue of origin, the self-organization process of organoids is uniquely manifested in three-dimensional culture systems, which reproduce biologically relevant cell-cell and cell-matrix interactions and results in the emergence of complex morphology [Ranga et al. (2014) *Adv Drug Deliv Rev* 70, 19-28]. Another important aspect of organoids is the possibility to model genetic disorders by making use of patient-derived induced pluripotent stem cells or by introducing disease mutations. Personalized medicine and cost-effective development of therapies for rare diseases are recent examples of the ongoing evolution of the field.

Although organoids have gained significant attention, there remain major challenges that prevent organoid models from achieving broader acceptance as a reliable bridge between conventional in vitro and in-vivo models, and a broader deployment in drug discovery pipelines. Today, there are no systematic ways of generating new organoids, and even tissues for which organoid models have been established are largely beset by the problem of lack of reproducibility. This is manifested by the fact that most organoids develop in a random manner, thereby acquiring inconsistent structures and molecular identities.

A number of reasons account for these limitations in this still emerging field. Most organoid protocols require the use of Matrigel™, an undefined tumour-derived matrix which provides the required three-dimensional context but also presents highly variable and uncontrolled properties [Kleinman & Martin (2005) *Semin Cancer Biol* 15, 378-386]. Over the last decade or so, the field of biomaterials engineering has progressed substantially to enable the development of engineered three-dimensional in vitro tissue models that can recapitulate in vivo cellular behaviour through the control of multiple microenvironmental cues [Langer & Tirrell (2004) *Nature* 428, 487-492; Lutolf et al. (2009) *Nature* 462, 433-441; Griffith & Swartz (2006) *Nature Reviews Molecular Cell Biology* 7, 211-224].

A cornerstone in all of these in vitro models is a three-dimensional scaffold functioning as an analogue of the instructive natural ECM. By breaking down the associated physiological complexity into an experimentally amenable number of distinct interactions, such ECM analogues are expected to bridge the gap between traditional 2D cell culture methods and labour-intensive animal models.

Over the last few years, synthetic biomatrices have been developed which contain some of the essential signals to mimic the biological character of natural ECMs [Lutolf et al. (2003) *Nat Biotechnol* 21, 513-518]. In contrast to other three-dimensional matrices used in cell biology such as collagen, Matrigel™ or fibrin that are made from naturally derived proteins, the biochemical and biophysical properties of the purely synthetic matrices can be modulated in a wide range and, most importantly, nearly independently from each other. This offers a versatile and powerful 'molecular toolbox' to probe the influence of extrinsic factors on cell fate in three-dimensional in a quantitative fashion.

However, important challenges in using organoid-based approaches to generate functional tissue remain Indeed, upon reaching a certain size organoids cease to grow further and develop a necrotic core. One of the reasons for such growth arrest is the lack of organoid vascularization resulting in oxygen and nutrient deprivation. Bioengineered approaches to manufacture de novo microvascularisation have, however, been limited by the lack of printing resolution [Miller et al. (2012) *Nat Mater* 11, 768-774], while the incorporation of endothelial cells in three-dimensional constructs has resulted in randomly oriented vessels without connection to any external vascular supply [Levenberg et al. (2005) *Nat Biotechnol* 23, 879-884; Freiman, A. et al. (2016) *Stem Cell Res Ther* 7, 015-0251].

Equally important, the random organization of organoids can be ascribed to a lack of external developmental and organizational cues which are critical in directing in-vivo tissues to pattern [Turner et al. (2016) *Bioessays* 38, 181-191], and often derive from spatially imposed morphogen gradients. The spontaneous patterning events seen in organoids, while bearing some hallmarks of the in vivo tissue from which they were derived, do not reproduce the ordered spatial morphology derived from precise cell-cell, cell-matrix and ultimately tissue-tissue interactions.

Microfluidic approaches have been successful in studying gradient—mediated cell specification [Demers et al. (2016) *Development* 143, 1884-1892], and have achieved some level of patterning of tissue explants [Zagorski et al. (2017) *Science* 356, 1379-1383], however the inherent technical difficulties in transposing these techniques to a controlled three-dimensional context have prevented their use with organoids.

More recent efforts to impose in-vivo-like interactions have focused on spontaneously fusing organoids derived under separate differentiation regimes [Birey et al. (2017) *Nature* 545, 54-59], however this process remains highly uncontrolled and it is currently not possible to couple conditions required for simultaneous growth of organoids of different fates.

The current inability to integrate these various elements is particularly relevant in the context of complex tissues such as brain or spinal cord. Despite recent advances, there is still a huge technological gap in the organoid field, and in the transposition of 2D differentiation and co-culture approaches to three-dimensional. Indeed, and there is therefore a pressing need to develop methods to systematically recreate the microenvironmental process and biological interactions occurring in developing tissues. Unlike for cells growing conventionally in 2D where it can be argued that the only relevant variables are morphogen identity and exposure time, to achieve ordered three-dimensional organoid model systems, it will be necessary to also modulate ECM composition and add elements of vascularization, three-dimensional positional information and tissue-tissue interactions.

SUMMARY

1. A device for the culture of cellular aggregates, the device comprising a three-dimensional network of interconnect vessels of a biocompatible liquid- and gas-permeable photo polymerised material, wherein the three-dimensional network is connected to a plurality of inlets and a plurality of outlets for the delivery of liquids, characterized in that defined vessels within the three-dimensional network are blocked, thereby defining at least one spatially segregated network within and structurally in contact with the three-dimensional network, wherein the at least one spatially segregated network is connected to a separate inlet and a separate outlet, allowing the supply of a liquid to a subregion within the three-dimensional network.
2. The device according to statement 1, wherein the space in between the vessels is filled with a hydrogel. Within such hydrogel cells can proliferate. The hydrogel may contain nutrients for the cells. The present of a hydrogel equally may provide additional physical strength to the device.
3. The device according to statement 2, wherein the hydrogel is a natural or synthetic hydrogel such as collagen, laminin, Matrigel™, hyaluronic acid, or PEG.
4. The device according to any one of statements 1 to 3, wherein the vessels have an outer diameter of between 20 and 200 µm.
5. The device according to any one of statements 1 to 4, wherein the vessels have an inner diameter of between 10 and 100 µm.
6. The device according to any one of statements 1 to 5, wherein the vessel walls have a thickness of between 5 and 50 µm.
7. The device according to any one of statements 1 to 6, wherein the polymerised material is gelatine, albumin or PEG-DA.
8. The device according to any one of statements 1 to 7, wherein the three-dimensional network has a volume of between 0.025 mm 3 to 10 $cm^3$.
9. The device according to any one of statements 1 to 8, wherein any point in the space in between the network is at most 200 lam away from a vessel.
10. The device according to any one of statements 1 to 9, which is a multiwell plate wherein each well comprises a three-dimensional network of interconnect vessels of a biocompatible liquid- and gas-permeable photo polymerised material.
11. A method for the design of a delivery of a liquid to a subregion of a multicellular aggregate comprising the steps of:
    Providing a three-dimensional network of interconnect vessels of a biocompatible liquid- and gas-permeable photo polymerised material, wherein the network is connected to a plurality of inlets and outlets for the delivery of liquids,
    defining a subregion in the network and determining which vessels in the network must be blocked to limit the delivery of liquid by an inlet and an outlet to the subregion,
    blocking the determined vessels to obtain the defined subregion thereby generating a spatially segregated network within the three-dimensional network.
12. A method for the cultivation of cells, comprising the steps of:
    providing a device according to any one of statements 1 to 10, or prepared by the method of statement 11,
    cultivating cells in the space between the vessels of the cells,
    delivering continuously or during specified time periods a liquid to the vessels in the subregion created by the blocking of vessels.
13. The method according to statement 12, wherein the liquid delivered to the vessels of the subregions comprises a morphogen.
14. The method according to statement 12 or 13, wherein the liquid delivered to the vessels of the subregions comprises a pharmaceutical compound.
15. The method according to any one of statements 12 to 14, wherein the cells are human pluripotent stem cells or differentiated derivatives thereof, cells of an immortalized cell line, or primary isolated cells.
16. The method according to any one of statements 12 to 15, wherein the vascular network contains two defined subregions each connected to a different inlet and outlet for the administration of different liquids.
17. The method according to any of statements 12 to 16, wherein the inner walls of the vascular wall are seeded with cells. These cells form a monolayer which coats the inner wall surface of the vessel wall.
18. The method according to statement 17, wherein the cells being seeded are endothelial cells, pluripotent stem cell derived endothelial progenitor cells, or mature endothelial cells.

BRIEF DESCRIPTION OF THE DRAWINGS

Figure Legends

FIG. 1A shows the complete device comprising a network (5) connected to an inlet (51) and an outlet (52) via respectively delivery chambers (53) and (54) which distributes media to the individual vessels, and collects media from the individual vessels. Blocking nodes in the network (5) result in spatially segregated subregions (1, 2, 3, 4), each connected to an inlet (11, 21, 31, 41) and an outlet (12, 22, 32, 42).

FIG. 1B is the device of FIG. 1A, in which portions of the network (5) have been omitted to show the spatial arrangement of the spatially segregated subregions (1, 2, 3, 4).

DETAILED DESCRIPTION

Figure 1A:
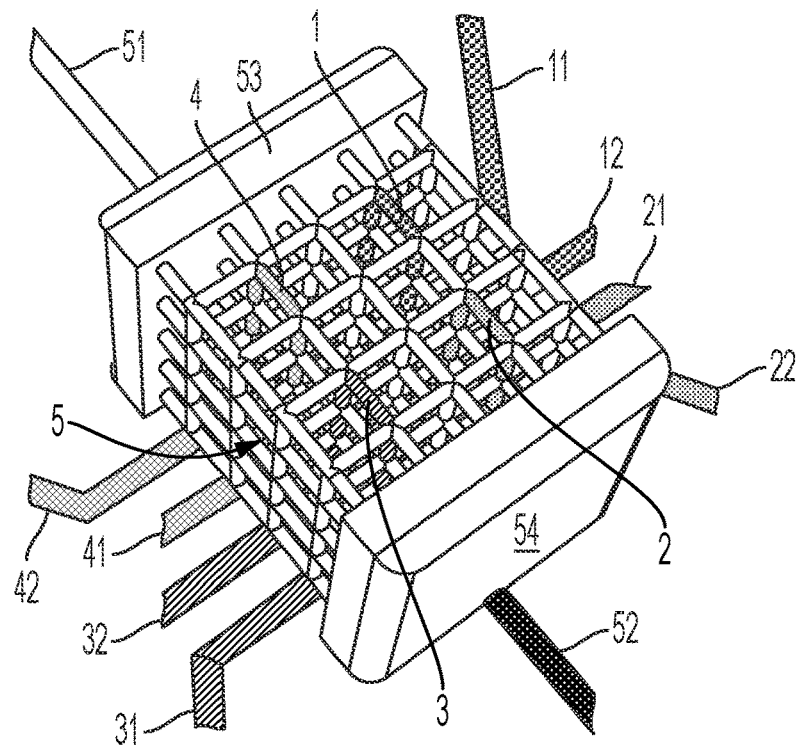
FIGS. 1A and 1B are examples of a design of the integrated combinatorial ECM-microvascularisation-patterning array.
Figure 1B:
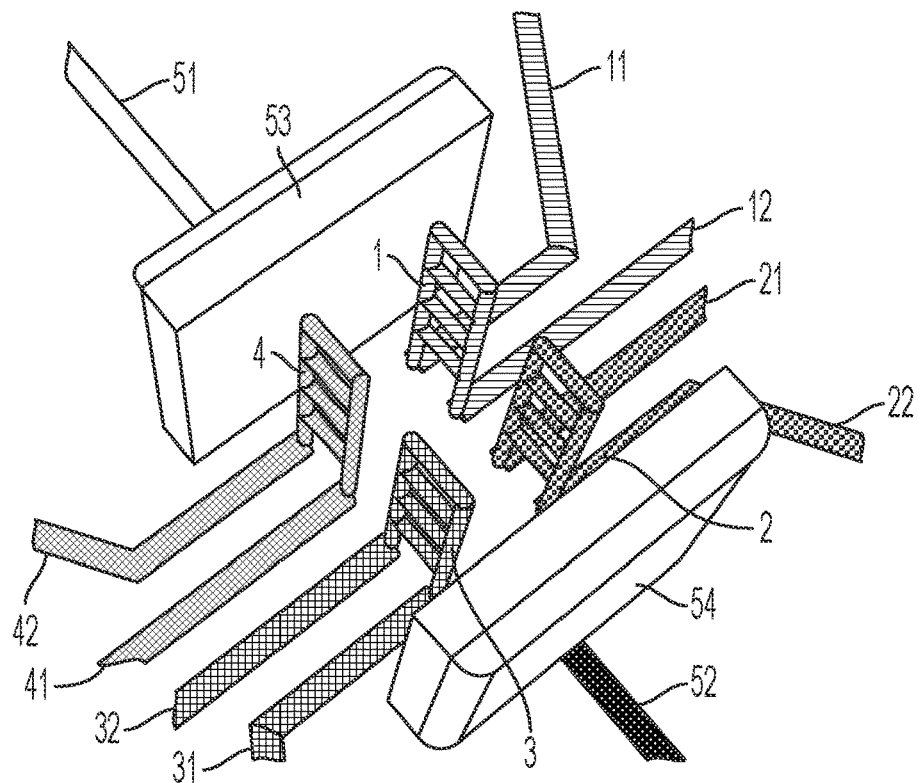

The present invention develops technology platforms and workflows which allow for the combinatorial modulation of design parameters specifically involved in organoid morphogenesis. These approaches involve the manipulation of the extracellular matrix and microenvironment, the enhancement of organoid growth via microvascularisation, and the imposition of spatially defined signalling allowing for robust patterning and tissue-tissue interactions. These highly reproducible organoid model systems are opening the door to wider applications of these tools in tissue engineering and stem cell biology.

Typically organoids are growth arrested after some time in culture, and will exhibit some stochastic patterning. To enhance growth and impose specific morphogen positional cues, a second aspect of the invention relates to the development of a microfluidic chip which allows for microvascularisation and localized morphogen delivery.

To determine in a systematic way how spatially defined inputs can enhance the patterning and maturation of these organoids features of the microfluidic chip are integrated into a multiplexed customized device and interfaced with an automated liquid handling robotics equipment capable of generating in a combinatorial manner extracellular matrices with a variety of properties (combinatorial materials microarray platform). Additionally, an aspect of the invention involves the co-culture of two different organoids in spatially defined locations, which allows for the possibility to investigate whether coupled growth of both organoid systems will enhance fate, morphogenesis and maturation of the individual organoids. Controlled interaction between these two organoids may lead to the recapitulation of native interactions between tissues.

The invention relates to devices for the culture of cellular aggregates comprising a three-dimensional network of interconnect vessels of a biocompatible liquid- and gas-permeable photo polymerised material, wherein the three-dimensional network is connected to a plurality of inlets and a plurality of outlets for the delivery of liquids, characterized in that defined vessels within the three-dimensional network are blocked, thereby defining at least one spatially segregated network within and structurally in contact with the three-dimensional network, wherein the at least one spatially segregated network is connected to a separate inlet and a separate outlet, allowing the supply of a liquid to a subregion within the three-dimensional network.

These devices differ significantly from the prior art and have several advantages. Different attempts have been made to supply three-dimensional cell aggregates with nutrients to the cells in the inner part of the cell aggregate. In these devices, a plurality of tubes of biocompatible material, optionally coated with cells, are horizontally arranged, and allow the passage of fluids through a cell aggregate. The coating with cells can be done as well on the inside of the tubes, by delivering a medium with suspended cells. Alternatively or in addition, the outside of the network can be contacted with cells which attach to the outside of the tubes, prior to growth of the cells leading to the organoid. When the delivery of different fluids is needed, either the medium is changed, or a separate set of tubes is provided, as shown in WO2016141137. Herein the two separate networks are typically symmetrically arranged to provide two media to a cell aggregate.

The photopolymerised material forms a grid which provides a mechanical support for the cells. When different media are supplied to a cell aggregates, and especially when a medium is to be supplied locally, the same grid can be used. Different experimental designs have no impact on the external structure of the grids, such that the cells always experience the same mechanical support of the grid.

The use of separate networks requires the generation of intertwined networks, which requires special precautions upon photopolymerisation of the networks.

The devices of the present invention can be made by a single production process, whereby depending on the type of spatially segregated network is required, certain tubes are sealed.

The devices of the present invention allow to design a set of networks which are structurally identical and which are internally different, such that a medium can be delivered at different sections of a cell aggregate. For example, a cell aggregate of tumours can be treated with a pharmaceutically active compound which is delivered in a network which is arranged as a shell around the cells. A difference in thickness of the shell can be used to determine when cells at the centre of the aggregate experience the effect of pharmaceutical active compound Whereas WO2016141137 allows the simultaneous delivery of two different media, the devices of the present invention can be designed to contain 3, 4, 5, 6, 8 10 or even more spatially separated networks.

The three-dimensional network can be printed for example in the shape of a cube or cuboid object, or as a sphere or ellipsoid element.

Blocking of the vessels is typically achieved by photopolymeration of the lumen of a vessel over a certain distance such that the flow of a liquid trough the vessel is prevented.

In specific embodiments, vessels are only blocked to provide one or more spatially segregated networks.

In addition, part of the vessels can be printed as solid vessels to provide additional support, or part of the vessels can be supplied upon use with a liquid which polymerizes within the vessel to provide mechanical support.

Furthermore, additional supporting vessels can extend through the holes in the three-dimensional network to suspend the network within.

To provide additional mechanical support the space in between the vessels can be filled with a hydrogel or a mixture of different hydrogels, such as collagen, laminin, hyaluronic acid, Matrigel™, or PEG.

In the devices of the invention, vessels typically have an outer diameter of about 20, 40, 60, 800, 100, 120, 140, 160, or 200 micrometre. The vessels within the device may all have the same outer diameter. In particular embodiments, 5%, 10%, 25% or 50% may have an outer diameter which differs from the average outer diameter. For example vessels on the outside of the vessel may have a wider outer diameter, and a thicker wall to provide additional mechanical support. Wall thickness also allows the tuning of diffusion speed, with thicker walls providing slower diffusion.

In the devices of the present inventions typically have inner diameter of between 10 and 100 µm, for example about 10, 20, 30, 40, 50, 60, 70, 80, 90 or 100 µm.

In the devices of the present invention vessel walls typically have a thickness of between 5 and 50 µm, 5, 10, 20, 30, 40, or 50 μm. The thickness can vary locally within the network, for example to provide additional physical strength, or to influence locally the perfusion of the wall.

The devices of the present invention can be made by different polymerised materials such as PEG-acrylate, PEG-diacrylate, gelatine, methacrylate, propylene fumarate derivatives, cross-linkable PVA derivatives, hyaluronic acid derivatives, dextran-methacrylate.

The volume of the three-dimensional network in the devices can range from between 0.025 mm 3 to 10 cm$^3$.

In the devices of the present invention typically any point in the space in between the network is at most 200 μm away from a vessel, to allow diffusion of nutrients and gasses to cells within the network. Specific embodiments are envisaged wherein the distance is bigger to create a local environment with limited oxygen and nutrient supply. However such environment can be equally obtained when vessels are blocked upon production of the network, or when a spatially separated network is not irrigated anymore or filled with a polymerisable material.

The devices of the present invention can be multiwell plates wherein each well comprises a three-dimensional network of interconnect vessels of a biocompatible liquid- and gas-permeable photo polymerised material.

Whereas different shapes and types of networks can be generated, a plurality of networks will typically be identical with the exception of the number and location of blocked vessels. In this way a highly reproducible setting can be obtained wherein differences in cell aggregates are attributed to differences in the spatial networks, and/or media delivered via the spatial networks.

The invention further relates to methods for the design of a delivery of a liquid to a subregion of a multicellular aggregate comprising the steps of:
  Providing a three-dimensional network of interconnect vessels of a biocompatible liquid- and gas-permeable photo-polymerised material, wherein the network is connected to a plurality of inlets and outlets for the delivery of liquids, defining a subregion in the network and determining which vessels in the network must be blocked to limit the delivery of liquid by an inlet and an outlet to the subregion,
  blocking the determined vessels to obtain the defined subregion thereby generating a spatially segregated network within the three-dimensional network.

The invention further relates to methods for the cultivation of cells, comprising the steps of:
  providing a device as described above,
  cultivating cells in the space between the vessels of the cells,
  delivering continuously or during specified time periods a liquid to the vessels in the subregion created by the blocking of vessels.

The liquid delivered to the vessels of the subregions can e.g. comprise a morphogen, pharmaceutical compound, a toxin, an antibody.

Cells can be pluripotent stem cells or differentiated derivatives thereof (human or murine), somatic stem cells or differentiated derivatives thereof, cells of an immortalized cell line or primary isolated cells In a specific embodiment the vascular network contains two defined subregions each connected to a different inlet and outlet for the administration of different liquids.

Examples

Example 1. Microvascular Perfusion and Patterning System for Controlled Organoid Morphogenesis To maintain sufficient diffusion of oxygen, nutrients, and waste products most cells in vivo lie within 100-200 μm of a capillary. In order to recapitulate this aspect of tissue physiology and enhance the growth and scale of organoids by maintaining cell viability throughout the growing construct, a microfluidic device is developed which allows for the imposition of medium perfusion via three-dimensional printed microvasculature. In a second step, this device is modified in order to gain the capability of imposing morphogen point sources, in order to achieve organoid patterning. The device comprises three elements: a network of hollow microvessels composed of a diffusible hydrogel, a secondary hydrogel filling the space within this network where organoids are grown, and a chip-based platform which allows for external perfusion of cell culture medium.

A microvascular grid is designed which can provide nutrients and oxygen within the required diffusion limits, and within the volumetric space required for organoid growth. As a starting point the grid has 150 μm vessel-to-vessel distance, and a total volume of 1 mm$^3$. This design is implemented in the SolidEdge CAD program, and is rendered fully parametric in order to rapidly change dimensions as required in further experiments. The geometrical complexity of the design and the requirements for accurate fabrication scales ranging from 10 μm (vessel wall thickness) to 1000 μm makes a two-photon laser scanning photopolymerization (2P-LSPP) approach the preferred technology for this purpose. In multiphoton excitation, a fluorescent molecule excitation occurs only when two or more photos of excitation light are absorbed at the same time; because excitation occurs only where photons coincide, the excitation light is not attenuated by fluorophore absorption above and below the point of focus, thereby enabling photopolymerisation of the material only in the specified focal point. This allows for the three-dimensional printing of any designed geometry, with maximal fidelity.

In principle, any photopolymerisable material can be used with any 2-photon microscope or printing system. In pilot experiments gelatine/albumin as well as a PEG-DA/Irgacure 369 combinations as a polymerization precursor to print a 1 mm$^3$ grid of intersecting micro-vessels. Horizontal image cross-sections obtained by a confocal microscopy indicate that the feature sizes possible with this process range from a few microns to a few millimetres.

Example 2. Integration of Microvascularised Grid into a Perfusable Chip

In order to use the photopolymerised microvascular grid for growing organoids, this grid is incorporated into a cell culture environment and connected to a perfusion system. To do so, an integrated platform is developed where the biocompatible, shaped grid structure is enclosed in a microfluidic chip which is connected to a perfusion system and in which organoids are seeded and cultivated. The microvascular grid thus provides perfusion of nutrients, oxygen and growth factors to the growing organoid. The grid material is composed of the photopolymerisable hydrogel, which is permeable to soluble molecules and gases. The space within and around the microvascular grid is typically filled with a second hydrogel, thereby providing a complete extracellular milieu with structural three-dimensional support to the growing organoid. The custom microfluidic chip is prototyped on a high-resolution Miicraft three-dimensional printer.

After the perfusion chip is fabricated via conventional three-dimensional printing, it is filled with photopolymer precursor. The polymeric microvascular grids are three-dimensional-printed using the dedicated laser three-dimensional printing system Photonic Professional GT (Nanoscribe GmbH) directly in the chip, and all unused precursor solution is then be removed via the perfusion system. By standard pipetting, the grids will are filled with hydrogel solution seeded with PSCs or PSC aggregates. The chip is then connected to the external high-precision syringe pump.

Example 3. Optimizing Perfusable Chip Design for Specific Applications

A variety of photo-initiator/polymer material combinations is tested, as well as polymerization regimes (e.g. scan speed, laser power, optical parameters of the system) on the Nanoscribe machine. Gelatine-BSA/Rose Bengal and PEG-DA/Irgacure 369 is found to be an example of a suitable polymer/photo-initiator pair for this application.

The secondary hydrogel component's primary function is as a three-dimensional matrix for supporting organoid growth. Additionally, the microvascular grid and secondary hydrogel function together as a composite material, whereby the secondary hydrogel also functions as a structural reinforcement to the grid. The optimization of this secondary material is application-specific and tailored to specific organoid types.

The perfusion chip with the integrated microvascular grid is connected to the external pump and the flow is tested. Optimal parameters for the perfusion flow (rate, positive/negative (suction) pressure) and topology of the microvascular network are determined as well as the smallest possible size of the microvessels.

The structural integrity and flow characteristics of the microvascular perfusion chip once the secondary hydrogel is added are evaluated in order to achieve both manufacturability and reliable organoid perfusion. The addition of the secondary hydrogel provides sufficient structural reinforcement to allow for a sufficiently high flow regime without disturbing network integrity. In order to guide the design optimization process for specific applications, computational FEA-CFD are used (Finite Element Analysis—Computational Fluid Dynamics).

Diffusion across the microvascular tubes is assessed, and the results of these computational simulations are validated by experimental data, using model fluorescently conjugated macromolecules (e.g. FITC-Dextran of various molecular weights). Structural mechanics simulations are used to model the interaction between the grid and the secondary hydrogel, to ensure that both structural (e.g. vessel wall thickness, vessel-to-vessel distance, material diffusivity) as well as fluidic parameters (e.g. flow rate) are concurrently optimized to generate a robust, leak-free and easy-to-use device, allowing for constant perfusion across the organoid-containing hydrogel.

Example 4. Validation of Perfusion System with Organoid Model Systems

The organoids are tested in the grid to demonstrate viability and enhanced growth of the tissue. Growth is assessed by time-lapse microscopy as well as with metabolic assays (e g Alamar Blue), and more complete characterization of the generated organoids is assessed by in-situ immunohistochemistry and with fluorescent reporter systems. Selected materials need to be biocompatible, and additionally, whatever residual unpolymerised material remains can be washed away in order not to affect biological function. The tested grid material (PEG-DA/Irgacure 369 composition) is not toxic and allows for significant organoid viability up to the currently tested 14 day endpoint.

Example 5. Manipulating Organoid Patterning with Microfluidic Morphogen Gradients and Point Sources While high-throughput microenvironmental discovery approaches can rapidly and efficiently explore a wide combinatorial space, and the incorporation of microvasculature can enhance organoid growth, one limitation remains that soluble factors and other signalling cues are applied to the organoids in a spatially uniform manner.

The microvasculature device is used to precisely probe the response of organoids to graded biomolecular signals in vitro. In particular, the extent to which spatially defined morphogen sources can provide a reference frame for organoid development is tested, thereby providing more robust patterning.

Figure 2:
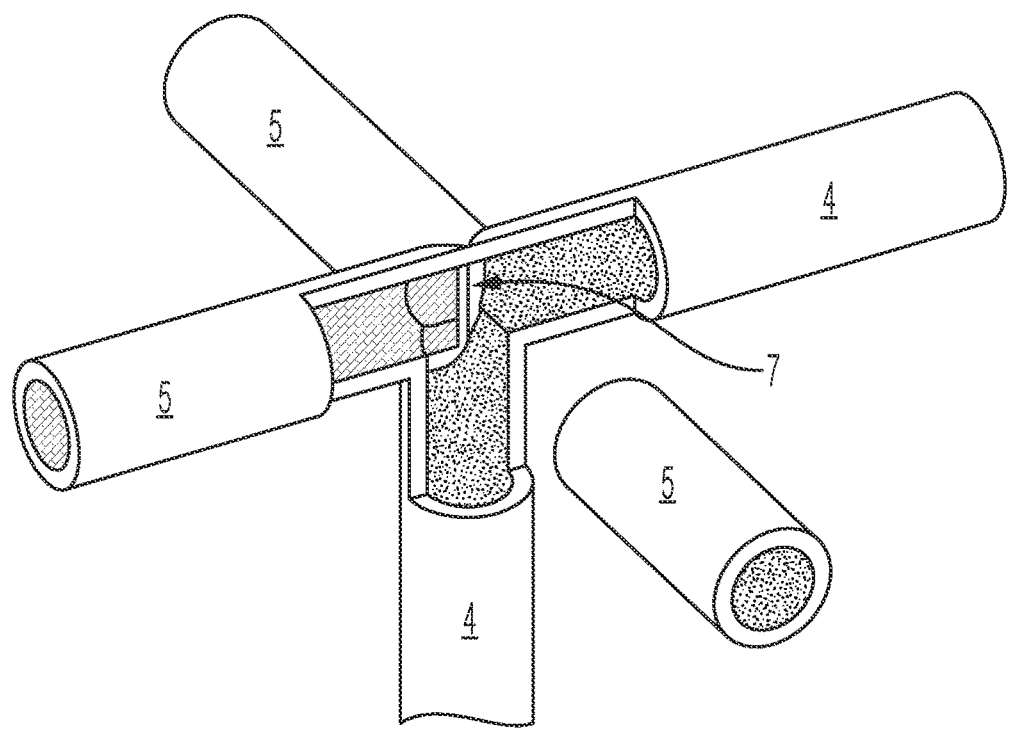
FIG. 2 is a detail of the three-dimensional network wherein the sealing (7) of the network (5) results in the creation of a spatially segregated subregion (4).
Figure 3:
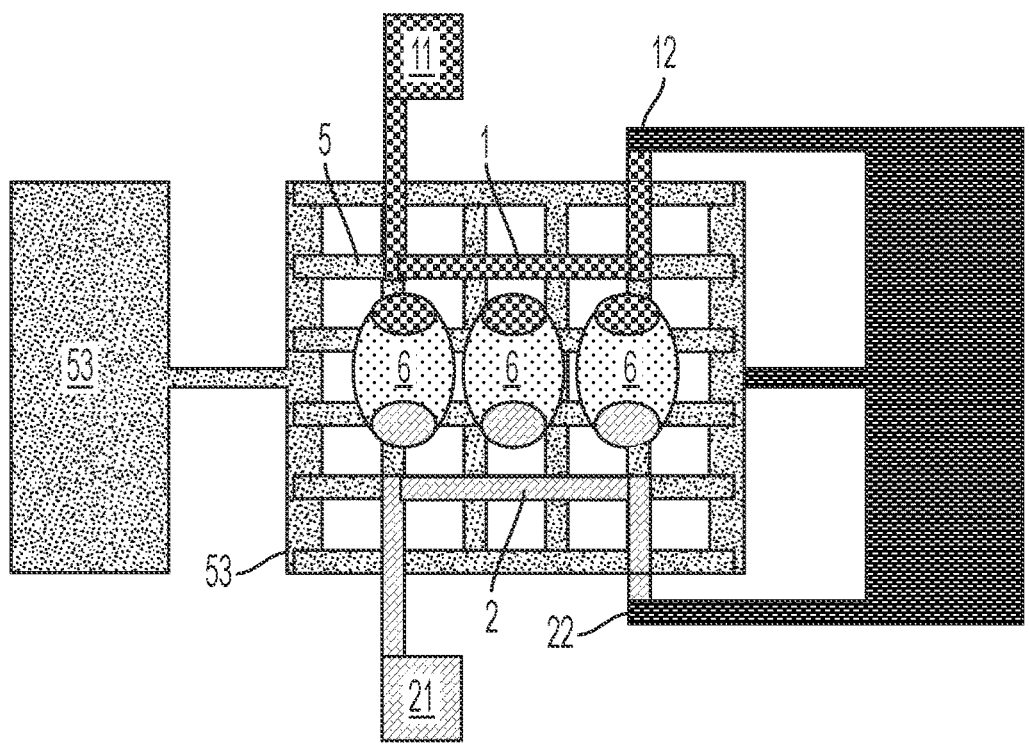
FIG. 3 shows an overview of a network wherein cell aggregates (6) receive basal medium from network (5) and whereby the cells experience the effect of morphogens provided by spatially segregated subregions (1) and (2).

The above described microvascularization grid is adapted. Instead of using a single inlet reservoir, additional, physically separated inlet reservoirs are added to the perfused grid, which will allow for the perfusion of multiple species. Concurrently, these inlets will be connected to topologically separate microvascular networks. This is be done by a modification to the polymerization scheme of the grid (FIG. 2): instead of designing all microvessels to freely communicate with each other, parts of the network are blocked by polymerizing the material in the centre of the vessel, thereby directing liquid flow into spatially segregated regions. Therefore, this provides a natural extension of the microvascularised system, by maintaining the same basic configuration of the system, while allowing for multiple inputs.

Using this principle, it is therefore conceivable that every two nodes of the microvasculature can function as an effective morphogen point source, as long as there is a path through the network to create a closed loop. Because species are diffusing through the walls of the microvessels in a complex three-dimensional configuration, the design of the morphogen sources is evaluated by computational analysis to quantify profiles and concentrations in three-dimensional space, and is validated experimentally using model fluorescent macromolecules and proteins.

The concept of the invention is illustrated with a highly simplified matrix with a volumetric space of 1 mm$^3$ with a 5×5 node grid space. By blocking the appropriate nodes, this leads to tractable and biologically relevant 2-way or 4-way point source configurations, which allows for the specification of orthogonal axes within an organoid. In order to test how directed factors could affect asymmetric fate specification in an organoid, the most promising combinations of matrix conditions/cellular compositions identified above are used as starting point and validated in the perfusion chip for each organoid. The dynamic manipulation of signalling factors using customized microfluidic tools allows for more controllable and realistic generation of developmental patterning.

The use of 2-photon polymerization approach and three-dimensional printing of the supporting chip ensures that design modifications based on new biological data as well as on computational simulations can be easily and rapidly prototyped and implemented into new design iterations.

Example 6. Multiplexed Platform Design

A platform with multiple microvascular grids is designed to reside in a custom-designed multi-well plate (e.g. 96 well), thereby providing a compact cell culture environment. Using the 2-photon laser three-dimensional printing system, the above grid design is reproduced in the new multiplexed setting, whereby each well contains a perfusable microvascularisation grid.

In a first iteration, the design of the plate incorporates a single perfusion inlet, which is connected to the inlet of each well of the plate via channels within the plate. A connecting channel between the inlet of the well and the inlet of the perfusion chip is generated during printing of the microvascular grid. A similar system is used to remove used medium, linking the outlet of the chip to the outlet channel of the plate via a hydrogel-based channel within the well. In this way, a common basal medium is perfused through all grids, and used media which will have perfused the organoids within the grids is gathered through a manifold to the common waste outlet. Perfusion via positive pressure at the inlet or negative pressure (vacuum) at the outlet is explored. An important aspect of this design is the benchmarking of this multiplexed design with previous single-well designs, which should ensure that expected enhanced organoid homogeneity and growth are reproduced.

In a second iteration, spatially defined morphogen point sources are added into the multiplexed design. To optimize the use of space, as well as to allow for at least four independent medium compositions per well, advantage is taken of the space around the round well to create "side wells" which are linked to the microvascular grid within the main well. The main advantage of this configuration is that each of these side wells is individually addressable by the liquid handling robot, thereby permitting a very flexible medium perfusion regime design within a single plate. The integration of this multiplexed grid plate with the automated materials microarray platform ensures that the anticipated advantages of microvascularization and patterning can be fully realized in the context of systematic ECM array generation.

Example 7. Systematic Mapping of Symmetry-Breaking Events in Developing Organoids An important advantage of such a multiplexed platform is to investigate in a systematic manner the symmetry-breaking events occurring over the course of organoid development. Experiments are initially performed with a 2-way morphogen source configuration, and, based on these results, determine the necessity of adding a further orthogonal signalling axis and map in a systematic way the requirements for spatial signalling at each symmetry-breaking developmental checkpoint.

The generation of biomimetic disease models, and particularly the implementation of these assays in a format amenable to high-throughput screening opens new avenues for drug discovery.

The ability to create arrays of highly reproducible, microvascularised and patterned organoids is a major contribution in the art. In particular, the ability to generate heterotypic organoids changes the organ-on-chip field, where current approaches are largely focused on building separate compartments for each organoid.

The invention claimed is:

1. A device for the culture of cellular aggregates, the device comprising
   a three-dimensional network of interconnected vessels of a biocompatible liquid-and gas-permeable photo-polymerized material, wherein:
   the three-dimensional network is connected to a plurality of inlets and a plurality of outlets for the delivery of liquids;
   lumens of defined vessels selected from the interconnected vessels within the three-dimensional network are blocked to limit the delivery of liquid by one of the plurality of inlets and one of one of the plurality of outlets to a subregion of the network, thereby defining at least one spatially segregated subregion within and in contact with the three-dimensional network; and
   the at least one spatially segregated subregion of the network is connected to another inlet of the plurality of inlets and another outlet of the plurality of outlets, allowing a supply of a liquid to the subregion within the three-dimensional network.

2. The device according to claim 1, wherein spaces between the interconnected vessels is filled with a natural or synthetic hydrogel.

3. The device according to claim 2, wherein the hydrogel is selected from the group consisting of collagen, laminin, a tumour-derived matrix, hyaluronic acid, and polyethylene glycol (PEG).

4. The device according to claim 1, wherein the interconnected vessels have outer diameters of from 20 μm to 200 μm.

5. The device according to claim 1, wherein the interconnected vessels have inner diameters of from 10 μm to 100 μm.

6. The device according to claim 1, wherein walls of the interconnected vessels have a thickness of from 5 μm to 50 μm.

7. The device according to claim 1, wherein the photopolymerized material is gelatin, albumin, or PEG-DA.

8. The device according to claim 1, wherein the three-dimensional network has a volume from 0.025 mm 3 to 10 $cm^3$.

9. A method for the cultivation of cells, the method comprising:
   providing a device according to claim 1;
   cultivating cells in spaces between the interconnected vessels of the three-dimensional network; and
   delivering continuously or during specified time periods a liquid to the subregion of the three-dimensional network.

10. The method according to claim 9, wherein the liquid comprises a morphogen or a pharmaceutical compound.

11. The method according to claim 9, wherein the cells are human pluripotent stem cells or differentiated derivatives thereof, cells of an immortalized cell line, or primary isolated cells.

* * * * *